United States Patent
Joseph et al.

(10) Patent No.: US 9,867,656 B2
(45) Date of Patent: Jan. 16, 2018

(54) MULTI-FUNCTION SURGICAL INSTRUMENTS

(71) Applicant: COVIDIEN LP, Mansfield, MA (US)

(72) Inventors: Daniel A. Joseph, Golden, CO (US); Brian R. Butcher, Longmont, CO (US); Amarsinh D. Jadhav, Islampur (IN); Purvish Soni, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 397 days.

(21) Appl. No.: 14/542,766

(22) Filed: Nov. 17, 2014

(65) Prior Publication Data

US 2016/0135868 A1    May 19, 2016

(51) Int. Cl.
*A61B 18/14* (2006.01)
*A61B 17/00* (2006.01)
*A61B 17/29* (2006.01)
*A61B 18/00* (2006.01)
*A61B 18/12* (2006.01)

(52) U.S. Cl.
CPC ............... *A61B 18/1445* (2013.01); *A61B 2017/00734* (2013.01); *A61B 2017/2912* (2013.01); *A61B 2018/00178* (2013.01); *A61B 2018/00196* (2013.01); *A61B 2018/00607* (2013.01); *A61B 2018/126* (2013.01); *A61B 2018/1253* (2013.01); *A61B 2018/1422* (2013.01); *A61B 2018/1455* (2013.01); *A61B 2018/1467* (2013.01)

(58) Field of Classification Search
CPC ...... A61B 2017/22075; A61B 18/1442; A61B 18/1445

See application file for complete search history.

(56) References Cited

U.S. PATENT DOCUMENTS

| 5,312,391 A | 5/1994 | Wilk |
| 5,318,589 A | 6/1994 | Lichtman |
| 5,324,254 A | 6/1994 | Phillips |
| 5,401,274 A | 3/1995 | Kusunoki |

(Continued)

OTHER PUBLICATIONS

Extended European Search Report corresponding to counterpart Int'l Appln. No. EP 15 19 1274.8 dated Oct. 28, 2016.

(Continued)

*Primary Examiner* — Ronald Hupczey, Jr.
*Assistant Examiner* — Bo Ouyang

(57) ABSTRACT

A surgical instrument includes a housing, an energizable member, a powered deployment assembly, and a cable assembly. The energizable member is configured to supply electrosurgical energy to tissue, and is movable between a storage position and a deployed position. The powered deployment assembly is configured to selectively move the energizable member between the storage position and the deployed position. The cable assembly having a cable coupled to the housing at a first end and having a plug coupled to the cable at a second, opposite end. The cable housing one or more first wires for selectively providing electrosurgical energy to the energizable member and one or more second wires for selectively providing power to the powered deployment assembly. The plug is configured to house a battery therein for powering the powered deployment assembly via the one or more second wires.

10 Claims, 7 Drawing Sheets

(56) References Cited

U.S. PATENT DOCUMENTS

| | | |
|---|---|---|
| 5,445,638 A | 8/1995 | Rydell et al. |
| 5,458,598 A | 10/1995 | Feinberg et al. |
| 5,556,397 A | 9/1996 | Long et al. |
| 5,735,873 A | 4/1998 | MacLean |
| 5,792,164 A | 8/1998 | Lakatos et al. |
| 5,893,863 A | 4/1999 | Yoon |
| 5,919,202 A | 7/1999 | Yoon |
| 6,113,596 A | 9/2000 | Hooven et al. |
| 6,156,009 A | 12/2000 | Grabek |
| 6,190,386 B1 | 2/2001 | Rydell |
| 6,270,497 B1 | 8/2001 | Sekino et al. |
| 6,299,625 B1 | 10/2001 | Bacher |
| 6,387,094 B1 | 5/2002 | Eitenmuller |
| 6,551,313 B1 | 4/2003 | Levin |
| 6,679,882 B1 | 1/2004 | Kornerup |
| 6,808,525 B2 | 10/2004 | Latterell et al. |
| 6,942,662 B2 | 9/2005 | Goble et al. |
| 7,033,356 B2 | 4/2006 | Latterell et al. |
| 7,063,699 B2 | 6/2006 | Hess et al. |
| 7,128,254 B2 | 10/2006 | Shelton, IV et al. |
| 7,232,440 B2 | 6/2007 | Dumbauld et al. |
| 7,367,976 B2 | 5/2008 | Lawes et al. |
| 7,402,162 B2 | 7/2008 | Ouchi |
| 7,445,621 B2 | 11/2008 | Dumbauld et al. |
| 7,510,562 B2 | 3/2009 | Lindsay |
| 7,588,570 B2 | 9/2009 | Wakikaido et al. |
| 7,658,311 B2 | 2/2010 | Boudreaux |
| 7,758,577 B2 | 7/2010 | Nobis et al. |
| 7,815,636 B2 | 10/2010 | Ortiz |
| 7,819,872 B2 | 10/2010 | Johnson et al. |
| 8,197,490 B2 * | 6/2012 | Pool .................. A61B 17/7004 606/105 |
| 8,257,352 B2 | 9/2012 | Lawes et al. |
| 8,353,437 B2 | 1/2013 | Boudreaux |
| 2002/0049442 A1 | 4/2002 | Roberts et al. |
| 2003/0090162 A1 | 5/2003 | Cornog et al. |
| 2003/0233099 A1 * | 12/2003 | Danaek .................. A61N 1/403 606/96 |
| 2004/0024433 A1 | 2/2004 | Roy et al. |
| 2004/0236326 A1 | 11/2004 | Schulze et al. |
| 2005/0012405 A1 | 1/2005 | Yajima et al. |
| 2005/0187547 A1 | 8/2005 | Sugi |
| 2006/0095033 A1 * | 5/2006 | Garabedian ........ A61B 18/1482 606/41 |
| 2007/0149968 A1 * | 6/2007 | Gonon ............... A61B 17/3203 606/45 |
| 2008/0215050 A1 | 9/2008 | Bakos |
| 2009/0125026 A1 | 5/2009 | Rioux et al. |
| 2009/0125027 A1 | 5/2009 | Fischer |
| 2009/0131974 A1 | 5/2009 | Pedersen et al. |
| 2009/0254084 A1 | 10/2009 | Naito |
| 2010/0185196 A1 | 7/2010 | Sakao et al. |
| 2010/0185197 A1 | 7/2010 | Sakao et al. |
| 2010/0268226 A1 * | 10/2010 | Epp .................... A61B 18/1492 606/48 |
| 2010/0292690 A1 | 11/2010 | Livneh |
| 2011/0087218 A1 | 4/2011 | Boudreaux et al. |
| 2011/0130757 A1 | 6/2011 | Horlle et al. |
| 2011/0264093 A1 | 10/2011 | Schall |
| 2012/0330351 A1 | 12/2012 | Friedman et al. |
| 2014/0046324 A1 | 2/2014 | Belson et al. |
| 2014/0066928 A1 * | 3/2014 | Bennett ............ A61B 17/32002 606/45 |
| 2014/0276797 A1 | 9/2014 | Batchelor et al. |

OTHER PUBLICATIONS

Partial European Search Report corresponding to counterpart Int'l Appln. No. EP 15 19 1274.8 dated Jun. 1, 2016.

\* cited by examiner

MULTI-FUNCTION SURGICAL INSTRUMENTS

BACKGROUND

Technical Field

The present disclosure relates to surgical instruments and, more particularly, to multi-function surgical instruments capable of operating in both a bipolar mode and a monopolar mode.

Background of Related Art

Bipolar surgical instruments, e.g., bipolar electrosurgical forceps, typically include two generally opposing electrodes charged to different electrical potentials for conducting energy therebetween and through tissue. Bipolar electrosurgical forceps utilize both mechanical clamping action and electrical energy to effect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue.

Monopolar surgical instruments, on the other hand, include an active electrode, and are used in conjunction with a remote return electrode, e.g., a return pad, to apply energy to tissue. Monopolar instruments have the ability to rapidly move through tissue and dissect through narrow tissue planes.

In some surgical procedures, it may be beneficial to use both bipolar and monopolar instrumentation, e.g., procedures where it is necessary to dissect through one or more layers of tissue in order to reach underlying tissue(s) to be sealed. Further, it may be beneficial, particularly with respect to endoscopic surgical procedures, to provide a single instrument incorporating both bipolar and monopolar features, thereby obviating the need to alternatingly remove and insert the bipolar and monopolar instruments in favor of one another.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

In accordance with the present disclosure, a surgical instrument is provided including a housing, an energizable member, a powered deployment assembly, and a cable assembly. The energizable member is configured to supply electrosurgical energy to tissue, and is movable between a storage position and a deployed position. The powered deployment assembly is configured to selectively move the energizable member between the storage position and the deployed position. The cable assembly having a cable coupled to the housing at a first end and having a plug coupled to the cable at a second, opposite end. The cable housing one or more first wires for selectively providing electrosurgical energy to the energizable member and one or more second wires for selectively providing power to the powered deployment assembly. The plug is configured to house a battery therein for powering the powered deployment assembly via the one or more second wires.

In an aspect of the present disclosure, the energizable member is coupled to an actuator disposed in the powered deployment assembly such that selective actuation of the actuator moves the energizable member between the storage position and the deployed position.

In another aspect of the present disclosure, the actuator includes a ferromagnetic material and wherein the powered deployment assembly further includes a magnet configured to actuate the actuator.

In still another aspect of the present disclosure, the magnet is an electromagnet and wherein the energy source in the plug is configured to selectively produce a magnetic field around at least a portion of the electromagnet.

In yet another aspect of the present disclosure, the powered deployment assembly includes a guide extending between a proximal portion and a distal portion thereof, the magnet being fixed to the distal portion and the actuator being slidably disposed on the proximal portion.

In still yet another aspect of the present disclosure, the powered deployment assembly further includes a biasing member disposed between the magnet and the actuator, the biasing member configured to bias the magnet away from the actuator.

In another aspect of the present disclosure, the surgical instrument further including a switch assembly operably coupled to the powered deployment assembly and to a source of electrosurgical energy such that when the switch is activated electrosurgical energy is supplied to the energizable member when the energizable member is in the deployed position.

In another aspect of the present disclosure, the powered deployment assembly includes a motor configured to drive movement of the energizable member between the storage position and the deployed position.

Another surgical instrument provided in accordance with the present disclosure includes a housing, an energizable member, a powered deployment assembly, and a switch assembly. The energizable member is configured to supply electrosurgical energy to tissue and is movable relative to the housing between a storage position and a deployed position. The powered deployment assembly is configured to selectively translate the energizable member between the storage position and the deployed position. The powered deployment assembly includes an electromagnet disposed in the housing and configured to be selectively energizable, an actuator disposed in the housing and movable along an axis between a proximal position and a distal position, the actuator being operably coupled to the energizable member, and a biasing member disposed between the electromagnet and the actuator to biased the electromagnet and actuator apart from one another. Energizing the electromagnet moves the actuator distally towards the electromagnet, thereby translating the energizable member to the deployed position. The switch assembly is disposed on the housing and is operably coupled to the powered deployment assembly for selectively energizing the electromagnet.

In an aspect of the present disclosure, the powered deployment assembly includes a guide extending between a proximal portion and a distal portion thereof, the electromagnet being fixed to the distal portion and the actuator being slidably disposed on the proximal portion.

In another aspect of the present disclosure, the guide includes at least one stopper, the at least one stopper configured to provide for controlled linear motion of the actuator.

In yet another aspect of the present disclosure, a cable assembly is coupled to the housing at a first end, and has a plug at a second, opposite end, the plug adapted to connect to an energy source for powering the powered deployment assembly.

In another aspect of the present disclosure, the plug houses a battery for powering the powered deployment assembly.

In still another aspect of the present disclosure, the switch assembly includes at least one sensor, the at least one sensor adapted to communicate with a source of electrosurgical energy to selectively supply electrosurgical energy to the energizable member when the energizable member is in the deployed position.

In accordance with the present disclosure, a surgical system is provided including a surgical instrument and an electrosurgical generator. The surgical instrument includes a housing, an energizable member, a powered deployment assembly, and a cable assembly. The energizable member is configured to supply electrosurgical energy to tissue, and is movable between a storage position and a deployed position. The powered deployment assembly is configured to selectively move the energizable member between the storage position and the deployed position. The cable assembly having a cable coupled to the housing at a first end and having a plug coupled to the cable at a second, opposite end. The cable housing one or more first wires for selectively providing electrosurgical energy to the energizable member and one or more second wires for selectively providing power to the powered deployment assembly. The plug is configured to house a battery therein for powering the powered deployment assembly via the one or more second wires. The electrosurgical generator is configured to generate electrosurgical energy, wherein the plug is operably coupled to the electrosurgical generator to selectively supply electrosurgical energy to the energizable member.

In an aspect of the present disclosure, the plug defines a plug housing configured to house the battery.

In another aspect of the present disclosure, the plug housing includes a housing door for selectively enclosing the battery inside the plug.

In yet another aspect of the present disclosure, the battery is selectively replaceable.

In still another aspect of the present disclosure, the battery is a 9V battery, although other suitable batteries or energy sources are also contemplated.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
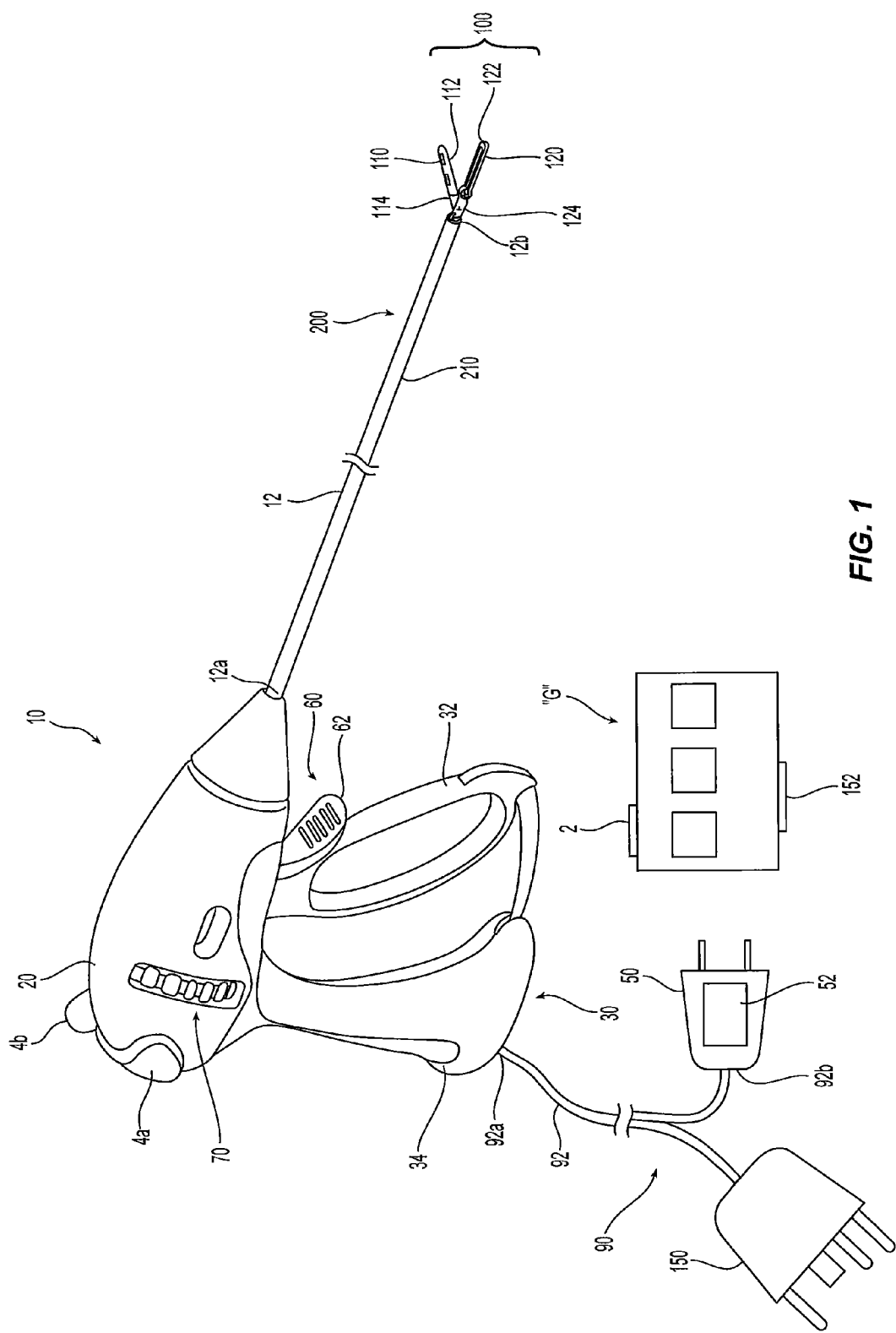
FIG. 1 is a perspective view of a surgical system provided in accordance with the present disclosure including an endoscopic surgical forceps and a generator.

Embodiments of the presently disclosed surgical instruments are described in detail with reference to the drawings, in which like reference numerals designate identical or corresponding elements in each of the several views.

Referring generally to FIG. 1, a forceps 10 is provided in accordance with the present disclosure. The forceps 10, as will be described below, is configured to operate in both a bipolar mode, e.g., for grasping, treating, and/or dissecting tissue, and a monopolar mode, e.g., for treating and/or dissecting tissue. Although the present disclosure is shown and described with respect to the forceps 10, the aspects and features of the present disclosure are equally applicable for use with any suitable surgical instrument or portion(s) thereof. Obviously, different connections and considerations apply to each particular instrument and the assemblies and/or components thereof; however, the aspects and features of the present disclosure remain generally consistent regardless of the particular instrument, assemblies, and/or components provided.

Continuing with reference to FIG. 1, the forceps 10 includes a housing 20, a handle assembly 30, a trigger assembly 60, a rotating assembly 70, a powered deployment assembly 80 (FIGS. 3 and 4), a cable assembly 90, an end effector assembly 100, and a monopolar assembly 200. Forceps 10 further includes a shaft 12 having a distal end 12b configured to mechanically engage end effector assembly 100 and a proximal end 12a that mechanically engages housing 20. The forceps 10 is operably coupled to a source of electrosurgical energy, such as, for example, an electrosurgical generator "G," using a cable 92 of the cable assembly 90. Cable 92 includes a first end 92a coupled to housing 20 and a bifurcated second, opposite end 92b coupled to a plug assembly having a monopolar plug 50 and a bipolar plug 150. Monopolar plug 50 is configured to releasably couple to a monopolar input 2 of generator "G," while bipolar plug 150 is configured to releasably couple to a bipolar input 152 of generator "G." Cable 92 includes wires (not shown) extending therethrough that have sufficient length to extend through the shaft 12 in order to provide electrical energy to end effector assembly 100, e.g., upon activation of bipolar activation switch 4a. One or more of the wires (not shown) of cable 92 extends through housing 20 in order to provide electrical energy to monopolar assembly 200, e.g., upon activation of monopolar activation switch 4b. The forceps 10 may be energized using other suitable power sources. In some embodiments, the forceps 10 may alternatively be configured as a battery-powered instrument.

Continuing with reference to FIG. 1, rotating assembly 70 is rotatable in either direction to rotate end effector assembly 100 and monopolar assembly 200 relative to housing 20. Housing 20 houses the internal working components of forceps 10.

Figure 2A:
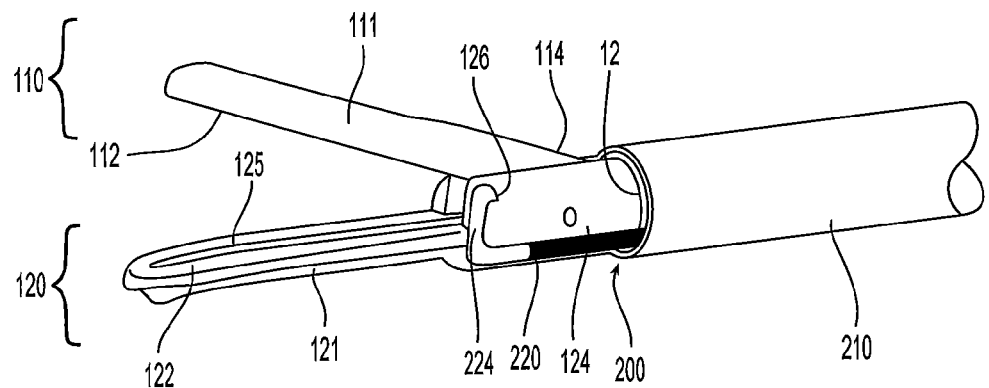
FIG. 2A is an enlarged, front, perspective view of an end effector assembly of the forceps of FIG. 1, wherein jaw members of the end effector assembly are disposed in a spaced-apart position and wherein a monopolar assembly is disposed in a storage position.
Figure 2B:
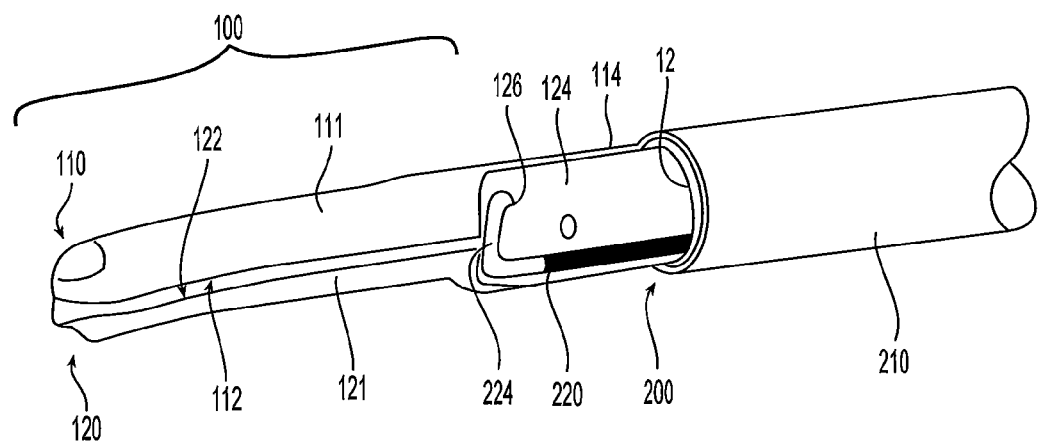
FIG. 2B is an enlarged, front, perspective view of the end effector assembly of FIG. 2A, wherein the jaw members are disposed in an approximated position and wherein the monopolar assembly is disposed in the storage position.
Figure 2C:
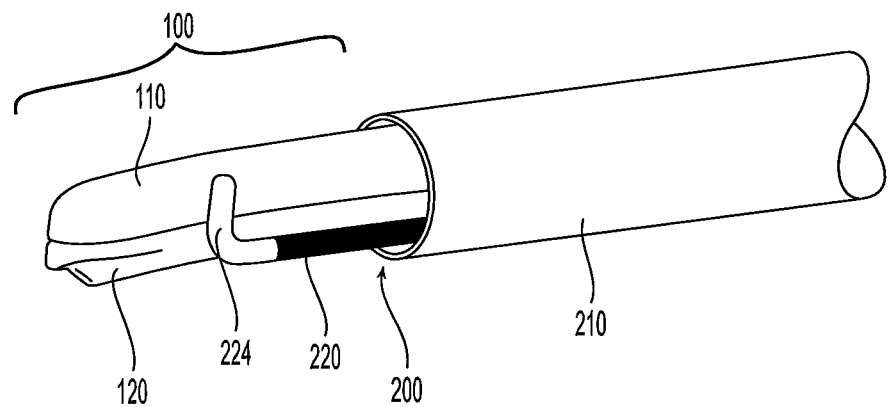
FIG. 2C is an enlarged, front, perspective view of the end effector assembly of FIG. 2A, wherein the jaw members are disposed in the approximated position and wherein the monopolar assembly is transitioning from the storage position to a deployed position.

Referring to FIGS. 2A-2B, end effector assembly 100 is attached at the distal end 12b of shaft 12 and includes a first jaw member 110 and an opposing second jaw member 120 pivotably coupled to one another. Each of the jaw members 110, 120 respectively includes a first jaw body 111 and a second jaw body 121 supporting a respective first electrically-conductive surface 112 and a second electrically-conductive surface 122, and a respective first proximally-extending jaw flange 114 and a second proximally-extending jaw flange 124. Flanges 114, 124 are pivotably coupled to one another to permit movement of jaw members 110, 120 relative to one another between a spaced-apart position (FIG. 2A) and an approximated position (FIG. 2B) for grasping tissue between electrically-conductive surfaces 112, 122. One or both of electrically-conductive surfaces 112, 122 are adapted to connect to electrosurgical generator "G," e.g., via the wires (not shown) of cable 92 (FIG. 1) and are configured to conduct energy through tissue grasped therebetween to treat, e.g., seal, tissue. More specifically, in some embodiments, end effector assembly 100 defines a bipolar configuration wherein electrically-conductive surface 112 is charged to a first electrical potential and electrically-conductive surface 122 is charged to a second, different electrical potential such that an electrical potential gradient is created for conducting energy between electrically-conductive surfaces 112, 122 and through tissue grasped therebetween for treating e.g., sealing, tissue. Bipolar activation switch 4a (FIG. 1) is operably coupled between electrosurgical generator "G" and electrically-conductive surfaces 112, 122, thus allowing the user to selectively apply energy to electrically-conductive surfaces 112, 122 of jaw members 110, 120, respectively, of end effector assembly 100.

End effector assembly 100 is designed as a unilateral assembly, i.e., where jaw member 120 is fixed relative to shaft 12 and jaw member 110 is movable relative to shaft 12 and fixed jaw member 120. However, end effector assembly 100 may alternatively be configured as a bilateral assembly, i.e., where both jaw member 110 and jaw member 120 are movable relative to one another and to shaft 12. In some embodiments, a knife channel 125 may be defined within one or both of jaw members 110, 120 to permit reciprocation of a knife (not shown) therethrough, e.g., upon actuation of a trigger 62 of trigger assembly 60, to cut tissue grasped between jaw members 110, 120.

Figure 2D:
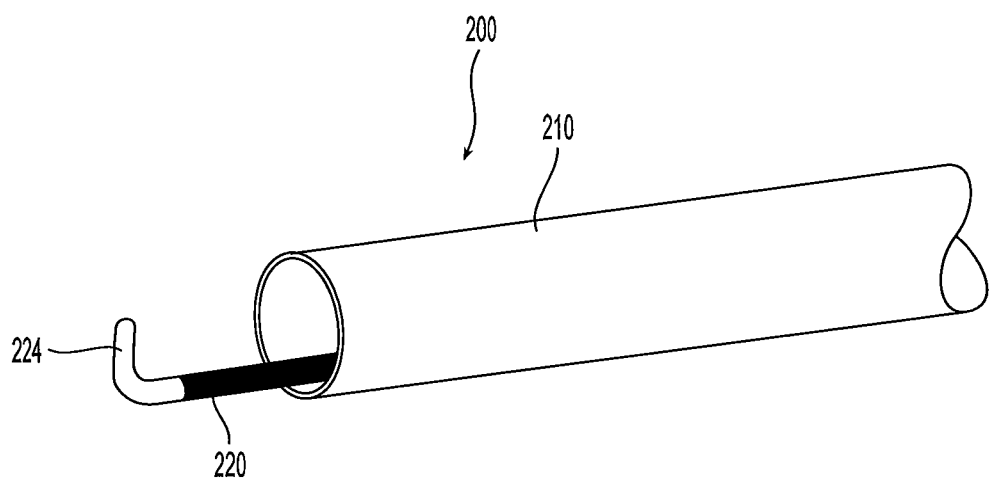
FIG. 2D is an enlarged, front, perspective view of the end effector assembly of FIG. 2A, wherein the monopolar assembly is disposed in the deployed position.

Referring to FIGS. 1-2D, monopolar assembly 200 includes an insulative sleeve 210, and an energizable member 220. Insulative sleeve 210 extends from the powered deployment assembly 80 (FIGS. 3-4), is slidably disposed about shaft 12, and is selectively movable about and relative to shaft 12 and end effector assembly 100 between a storage position (FIGS. 2A and 2B), wherein insulative sleeve 210 is disposed proximally of end effector assembly 100, and a deployed position (FIG. 2D), wherein insulative sleeve 210 is substantially disposed about end effector 100 so as to electrically insulate electrically-conductive surfaces 112, 122 of jaw members 110, 120, respectively.

Energizable member 220 extends from the powered deployment assembly 80 (FIGS. 3-4), through sleeve 210, and distally therefrom, ultimately defining an electrically-conductive tip 224. Energizable member 220 and, more specifically, electrically-conductive tip 224 thereof, functions as the active electrode of monopolar assembly 200. The one or more wires (not shown) extending from cable 92 through housing 20 (FIG. 1), are coupled to energizable member 220 to provide energy to energizable member 220, e.g., upon actuation of monopolar activation switch 4b (FIG. 1), for treating tissue in a monopolar mode of operation. Energizable member 220 is movable between a storage position (FIG. 2B) and a deployed position (FIG. 2D). In the storage position (FIG. 2B), electrically-conductive tip 224 of energizable member 220 is disposed within an insulated groove 126 defined within proximal flange 124 of jaw member 120, although other configurations are also contemplated. Insulated groove 126 electrically-insulates electrically-conductive tip 224 of energizable member 220 from electrically-conductive surfaces 112, 122 of jaw members 110, 120, respectively, and from surrounding tissue when disposed in the storage position. Alternatively, electrically-conductive tip 224 of energizable member 220 may only be insulated from surface 112. In such configurations, electrically-conductive tip 224 of energizable member 220 is capable of being energized to the same polarity as electrically-conductive surface 122.

In the deployed position (FIG. 2D), electrically-conductive tip 224 of energizable member 220 of monopolar assembly 200 extends distally from end effector assembly 100 while insulative sleeve 210 substantially surrounds end effector assembly 100. In this position, energy may be applied to electrically-conductive tip 224 of energizable member 220 to treat tissue, e.g., via activation of monopolar activation switch 4b (FIG. 1). Electrically-conductive tip 224 may be hook-shaped (as shown), or may define any other suitable configuration, e.g., linear, ball, circular, angled, etc.

As noted above, both insulative sleeve 210 and energizable member 220 are coupled to powered deployment assembly 80. Powered deployment assembly 80, as detailed below, is selectively actuatable to transition monopolar assembly 200 between its storage position (FIGS. 2A and 2B) and its deployed position (FIG. 2D). That is, powered deployment assembly 80 moves insulative sleeve 210 and energizable member 220 in conjunction with one another between their respective storage positions (collectively the storage position of monopolar assembly 200) and their respective deployed positions (collectively the deployed position of monopolar assembly 200).

With reference again to FIG. 1, handle assembly 30 includes a movable handle 32 and a fixed handle 34. Fixed handle 34 is integrally associated with housing 20 and movable handle 32 is movable relative to fixed handle 34.

Movable handle 32 is movable relative to fixed handle 34 between an initial position, wherein movable handle 32 is spaced from fixed handle 34, and a compressed position, wherein movable handle 32 is compressed towards fixed handle 34. A biasing member (not shown) may be provided to bias movable handle 32 towards the initial position. Movable handle 32 is ultimately connected to a drive assembly (not shown) disposed within housing 20 that, together, mechanically cooperate to impart movement of jaw members 110, 120 between the spaced-apart position (FIG. 2A), corresponding to the initial position of movable handle 32, and the approximated position (FIG. 2B), corresponding to the compressed position of movable handle 32. Any suitable drive assembly for this purpose may be provided.

Trigger assembly 60 includes trigger 62 that is operably coupled to a knife (not shown). Trigger 62 of trigger assembly 60 is selectively actuatable to advance the knife from a retracted position, wherein the knife is disposed proximally of jaw members 110, 120, to an extended position, wherein the knife extends at least partially between jaw members 110, 120 and through knife channel 125 (FIG. 2A) to cut tissue grasped between jaw members 110, 120.

Figure 3:
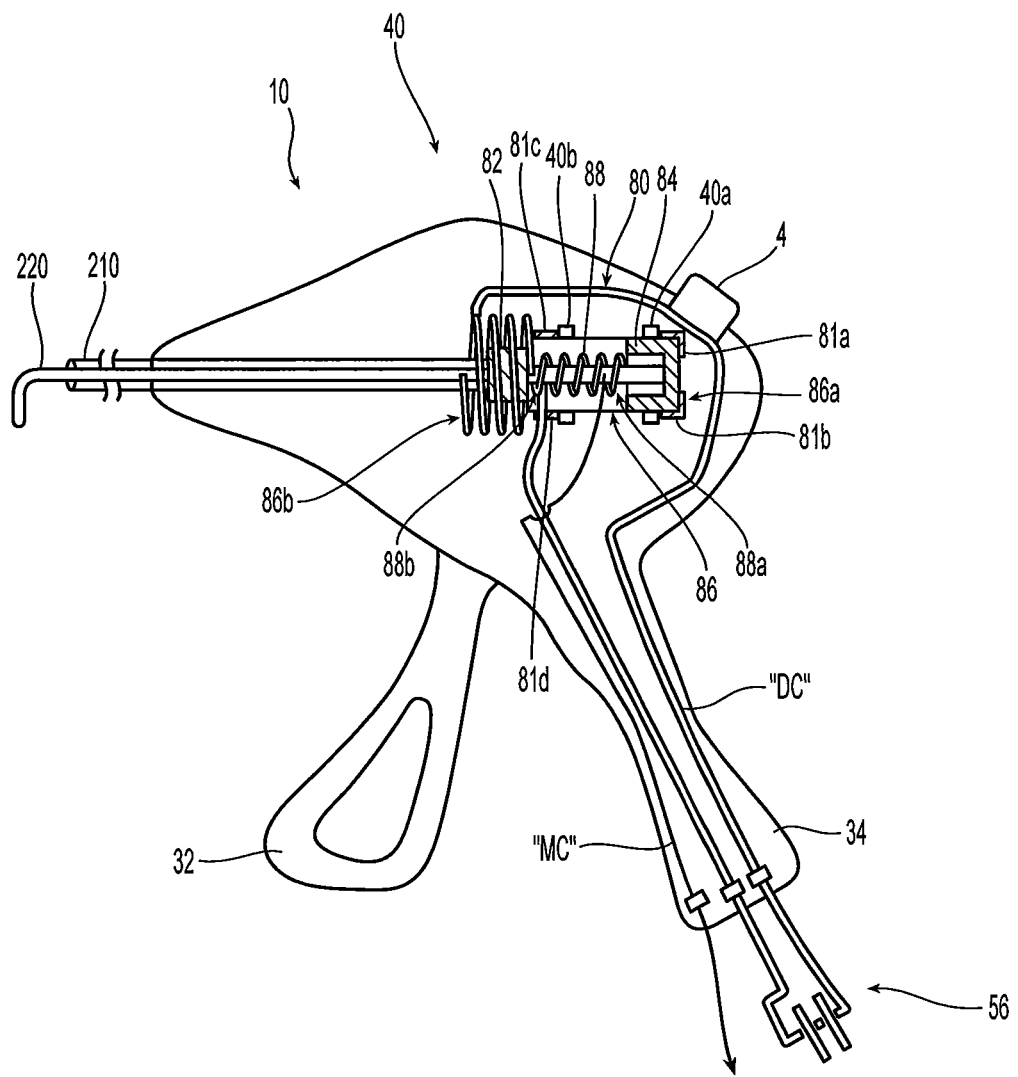
FIG. 3 is a side view of the proximal end of the forceps of FIG. 1 with a portion of the housing and internal components thereof removed to unobstructively illustrate the proximal end of the monopolar assembly and a deployment assembly for deploying the monopolar assembly, wherein the deployment assembly is disposed in an un-actuated condition corresponding to the storage position of the monopolar assembly.
Figure 4:
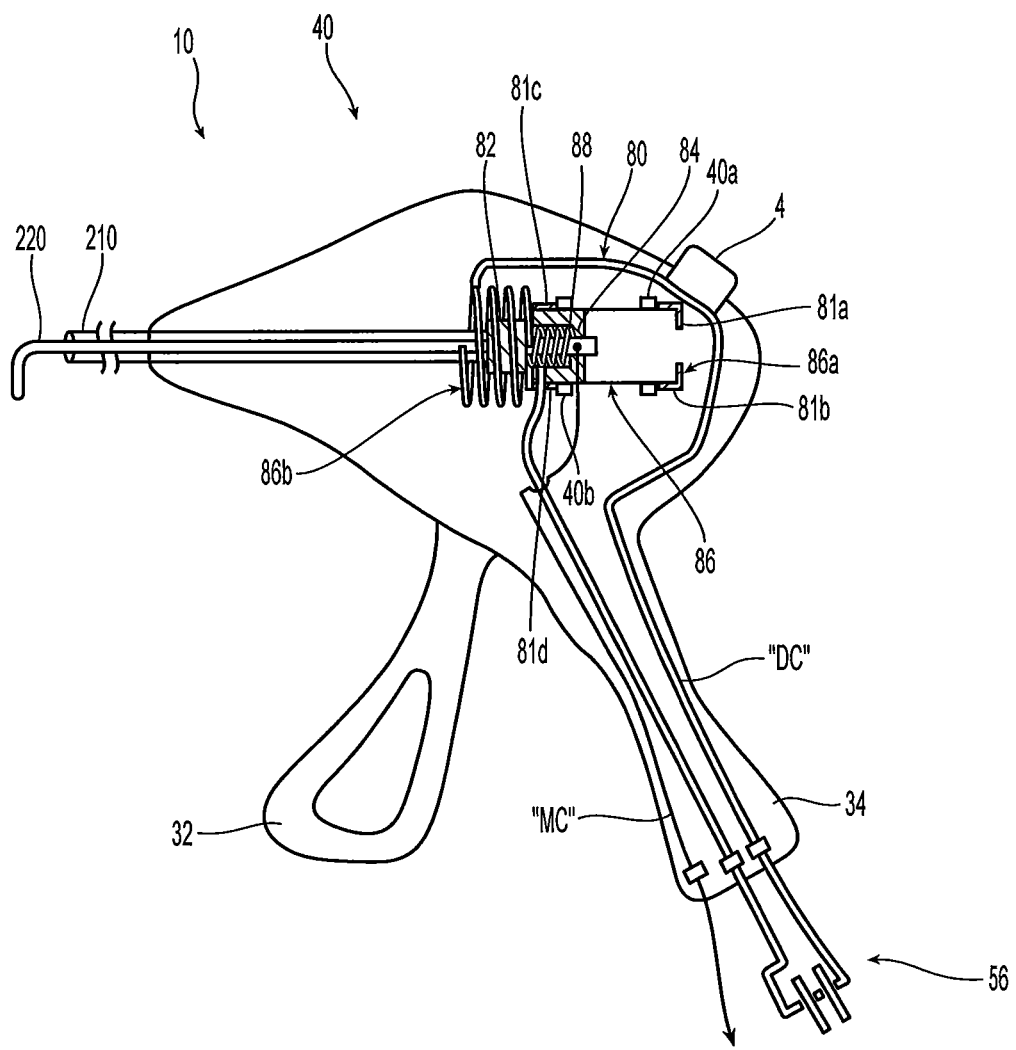
FIG. 4 is a side view of the proximal end of the forceps of FIG. 1 with a portion of the housing and internal components thereof removed to unobstructively illustrate the proximal end of the monopolar assembly and the deployment assembly, wherein the deployment assembly is disposed in an actuated condition corresponding to the monopolar assembly being disposed in the deployed position.

Referring to FIGS. 3-4, the powered deployment assembly 80 is configured for selectively transition monopolar assembly 200 between the storage position and the deployed position by translating insulative sleeve 210 and energizable member 220 in conjunction with one another (though not necessarily the same distance or simultaneously) between their respective storage positions and their respective deployed position. Powered deployment assembly 80, in one embodiment, includes a magnet, such as, for example, an electromagnet 82, an actuator 84, a guide 86, and a biasing member 88. Guide 86 extends longitudinally between a proximal portion 86a and a distal portion 86b and is configured to maintain the trajectory of actuator 84 parallel to or coaxial with a longitudinal axis. In some embodiments, electromagnet 82 is fixed to distal portion 86b and actuator 84 is slidingly disposed on proximal portion 86a. Other powered deployment assemblies are also contemplated, such powered deployment assembly 180 detailed below with respect to FIG. 5.

As shown in FIGS. 3-4, actuator 84 is coupled to insulative sleeve 210 and energizable member 220. As such, the distal translation of actuator 84 distally translates insulative sleeve 210 and energizable member 220. Similarly, the proximal translation of actuator 84 proximally translates insulative sleeve 210 and energizable member 220. When actuator 84 is adjacent proximal portion 86a of guide 86, monopolar assembly 200 is in the storage position (FIGS. 2A and 2B). When actuator 84 is adjacent distal portion 86b of guide 86, monopolar assembly 200 is in the deployed position (FIG. 2D).

Electromagnet 82 is coupled to monopolar activation switch 4b by way of a deployment circuit "DC" powered via an energy source, e.g., battery 56, electrosurgical generator "G," a standard wall outlet (not shown), etc. When monopolar activation switch 4b is activated, current is able to flow from the energy source through the deployment circuit "DC" to produce a magnetic field around at least a portion of electromagnet 82. In one embodiment, actuator 84 may be formed from a ferromagnetic material and therefore, becomes attracted to the magnetic field produced around at least a portion of electromagnet 82 such that actuator 84 is translated distally along guide 86 towards electromagnet 82 (FIG. 4) once monopolar activation switch 4b is activated and the magnetic field is produced. In alternative embodiments, it is contemplated that a ferrous alloy may be deposited on or incorporated into actuator 84. Functioning similar, when monopolar activation switch 4b is activated, the magnetic field is produced around at least a portion of electromagnet 82 and actuator 84 is translated distally along guide 86 towards electromagnet 82 (FIG. 4). The distal translation of actuator 84 from the proximal position (FIG. 3) to the distal position (FIG. 4) transitions monopolar assembly 200 from the storage position (FIGS. 2A and 2B) to the deployed position (FIG. 2D).

As shown in FIG. 3, biasing member 88 is disposed between electromagnet 82 and actuator 84, wherein a proximal portion 88a of biasing member 88 is fixed to actuator 84 and a distal portion 88b of biasing member 88 is fixed to electromagnet 82. Biasing member 88 is configured to bias electromagnet 82 apart from actuator 84. Thus, in order for actuator 84 to translate towards electromagnet 82, the magnetic field produced around at least a portion of electromagnet 82 has to be such that it overcomes the spring force of biasing member 88. On the other hand, when the magnetic field is insufficient to overcome the spring force of biasing member 88, e.g., when the magnetic field is removed, actuator 84 is urged proximally by the bias of biasing member 88 to its initial position relative to electromagnet 82 (see FIG. 3). Return of actuator 84 proximally from the distal position (FIG. 4) to the proximal position (FIG. 3) transitions monopolar assembly 200 from the deployed position (FIG. 2D) back to the storage position (FIGS. 2A and 2B).

In some embodiments, powered deployment assembly 80 may also include a stopper 81 configured to provide for a controlled linear motion of actuator 84, and thereby, insulative sleeve 210 and energizable member 220 of monopolar assembly 200. In some embodiments as shown in FIGS. 3-4, powered deployment assembly 80 may include a plurality of stoppers 81a-81d for similar purposes.

Continuing with FIGS. 3-4, housing 20 includes a switch assembly 40 disposed on guide 86. Switch assembly 40 is operably coupled to electrosurgical generator "G" by way of a monopolar circuit "MC" and is configured to selectively provide electrosurgical energy to energizable member 220. Switch assembly 40 includes a proximal sensor 40a adjacent proximal portion 86a of guide 86 and a distal sensor 40b adjacent distal portion 86b of guide 86. Sensors 40a, 40b are configured to identify and communicate the location of actuator 84, and thereby, the position of monopolar assembly 200 to electrosurgical generator "G." For example, when actuator 84 is adjacent proximal sensor 40a and, accordingly, monopolar assembly 200 is in the storage position (FIGS. 2A and 2B), proximal sensor 40a provides feedback to electrosurgical generator "G" such that electrosurgical generator "G" is signaled to withhold electrosurgical energy, such as, for example, a monopolar voltage-current from energizable member 220. Similarly, when actuator 84 is adjacent distal sensor 40b and, accordingly, monopolar assembly 200 is in the deployed position (FIG. 2D), distal sensor 40b provides feedback to electrosurgical generator "G" such that electrosurgical generator "G" is signaled to provide monopolar voltage-current to energizable member 220. In alternative embodiments, proximal sensor 40a and distal sensor 40b may be "On/Off" switches such that when actuator 84 is adjacent proximal sensor 40a, monopolar circuit "MC" is "Off" and electrosurgical generator "G" is unable to supply monopolar voltage-current to energizable member 220. Similarly, in this embodiment, when actuator 84 is adjacent distal sensor 40b, monopolar circuit "MC" is "On" and electrosurgical generator "G" is able to supply monopolar voltage-current to energizable member 220.

Figure 5:
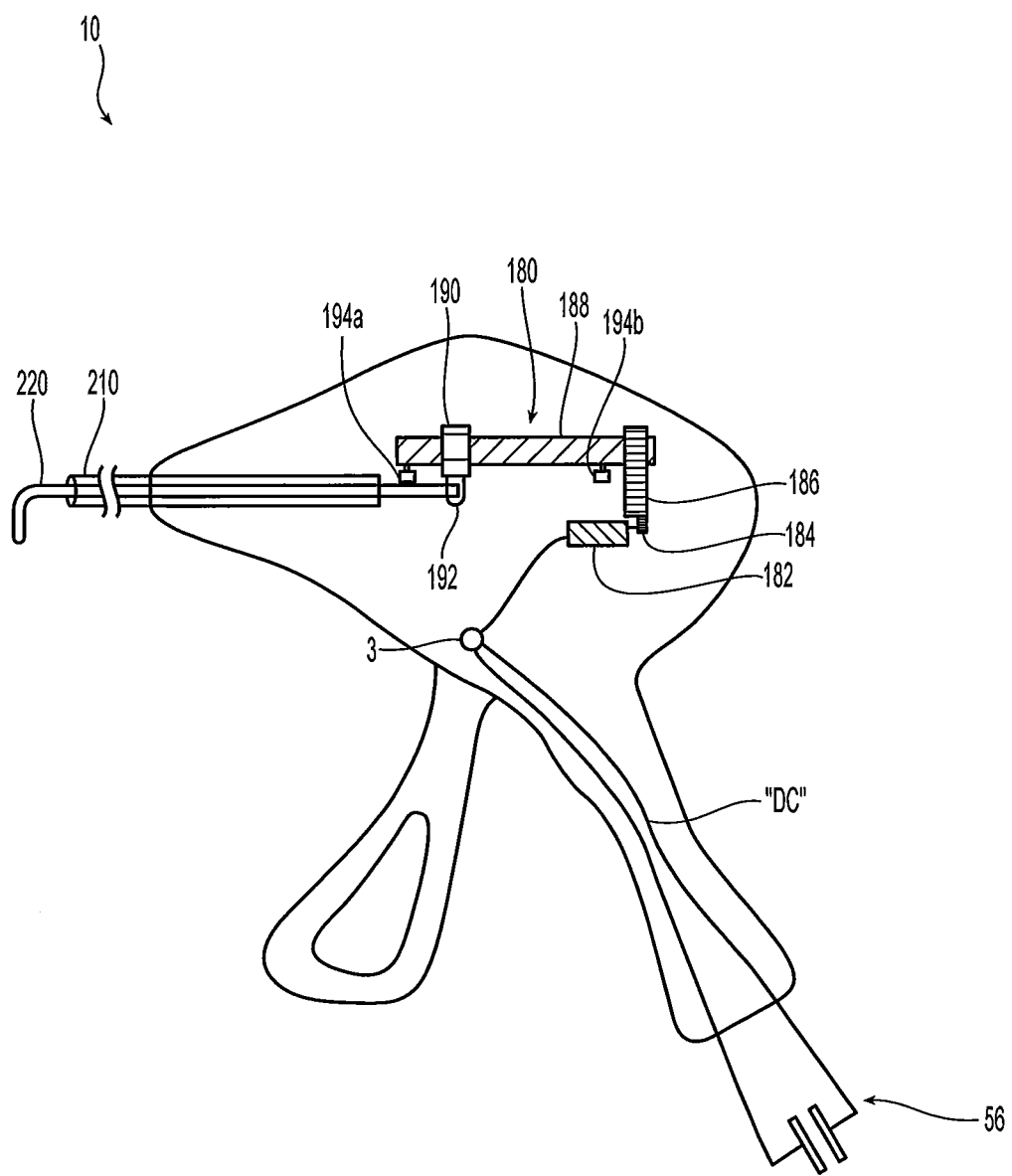
FIG. 5 is a side view of the proximal end of the forceps of FIG. 1 with a portion of the housing and internal components thereof removed to unobstructively illustrate the proximal end of the monopolar assembly and another deployment assembly for deploying the monopolar assembly.

Turning to FIG. 5, another powered deployment assembly 180 provided in accordance with the present disclosure is shown and described. Powered deployment assembly 180 is similar to powered deployment assembly 80 and is only described herein to the extent necessary to describe the differences in construction and operation thereof.

Powered deployment assembly 180 includes a motor 182 operatively coupled to a first gear 184, a switch 3, deployment circuit "DC," and an energy source, e.g., battery 56, electrosurgical generator "G," a standard wall outlet (not shown), etc. It is envisioned that switch 3 may be any suitable switch, such as, for example, a double pole double throw switch (DPDT). As detailed below, when switch 3 is activated, current is able to flow from the energy source through the deployment circuit "DC" to motor 182 to drive motor 182 to actuate first gear 184. First gear 184 is coupled to a second gear 186 such that actuation of first gear 184 affects a corresponding actuation of second gear 186.

Continuing with FIG. 5, a threaded rod 188 is operably coupled to second gear 186 and extends distally therefrom. A threaded nut 190 is operably disposed about threaded rod 188. Threaded nut 190 includes an attachment member 192 configured for coupling threaded nut 190 to monopolar assembly 200 (FIGS. 2A-2D), e.g., insulative sleeve 210 and/or energizable member 220. In operation, upon driving of motor 182, first gear 184 is actuated to actuate second gear 186 which, in turn, rotates threaded rod 188, thereby translating threaded nut 190 along threaded rod 188.

In use, as threaded nut 190 is translated along threaded rod 188, insulative sleeve 210 and energizable member 220 are likewise translated between their respective storage positions (FIGS. 2A and 2B) and their respective deployed positions (FIG. 2D), thus transitioning monopolar assembly 200 (FIGS. 2A-2D) between the storage and deployed positions. More specifically, in embodiments where switch 3 is a DPDT switch, for example, actuating switch 3 in a distal direction drives motor 182 in a "forward" direction to rotate threaded rod 188 in a first direction such that threaded nut 190 is translated distally to deploy monopolar assembly 200 (FIGS. 2A-2D), while actuating switch 3 in a proximal direction drives motor 182 in a "reverse" direction to rotate threaded rod 188 in a second, opposite direction such that threaded nut 190 is translated proximally to retract monopolar assembly 200 (FIGS. 2A-2D). However, the opposite is also envisioned as are other suitable switches and/or configurations thereof.

In some embodiments, threaded rod 188 further includes a distal stopper 194a and a proximal stopper 194b. Although FIG. 5 is shown with just two stoppers 194a, 194b, it is envisioned that powered deployment assembly 180 include any suitable number of stoppers. Stoppers 194a and 194b are configured to limit the translation of threaded nut 190 along the longitudinal axis of threaded rod 188 to define a travel length suitable for deploying and retracting monopolar assembly 200 (FIGS. 2A-2D).

Figure 6A:
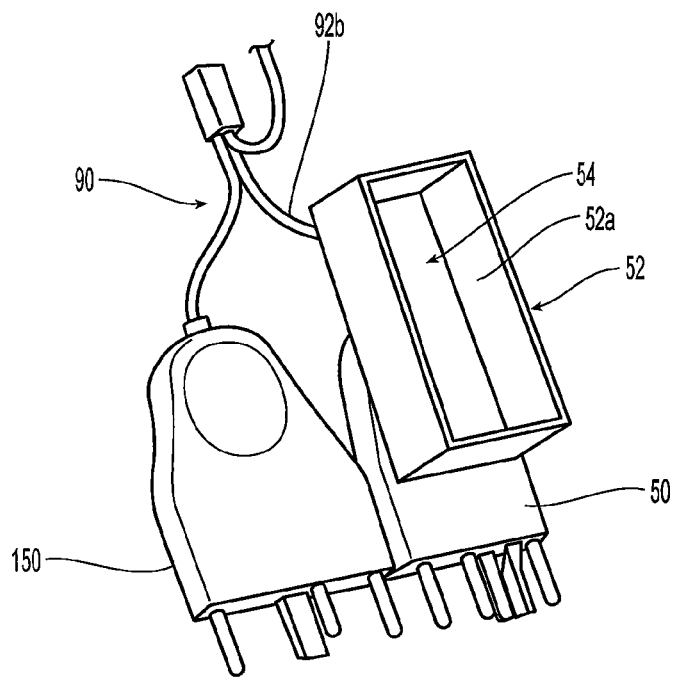
FIG. 6A is a perspective view of the proximal end of a cable assembly and plug assembly of the forceps of FIG. 1.
Figure 6B:
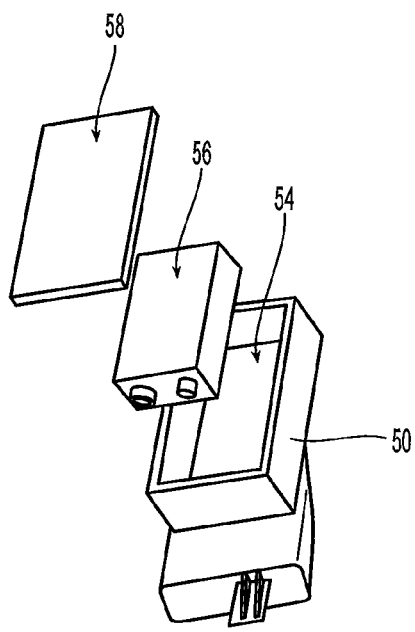
FIG. 6B is an exploded, perspective view of a monopolar plug of the plug assembly of FIG. 6A.
Figure 6C:
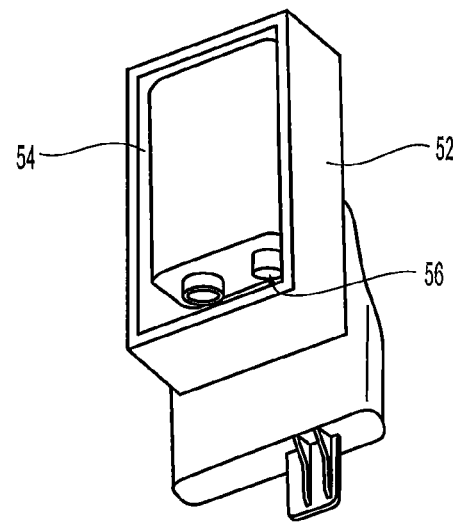
FIG. 6C is a perspective view of the monopolar plug of FIG. 6B with a battery received therein and the cover removed.

Turning now to FIGS. 6A-6C, in conjunction with FIG. 1, cable assembly 90, as mentioned above, includes a bifurcated second end 92b coupled to a plug assembly having a monopolar plug 50 and a bipolar plug 150. In some embodiments, monopolar plug 50 includes a plug housing 52 having an inner surface 52a. Inner surface 52a defines a compartment 54 configured for housing battery 56 which, as noted above, may be the energy source utilized for powering powered deployment assemblies 80, 180 (FIGS. 3-4 and 5, respectively), or any other suitable powered deployment assembly. In some embodiments, compartment 54 includes a rectangular cross-section, as shown in FIGS. 6A-6C. However, it is contemplated that compartment 54 may include any cross-section suitable for housing battery 56, e.g., depending upon the configuration, type, dimensions, etc. of battery 56.

Battery 56, as detailed above, forms part of deployment circuit "DC" (FIGS. 3-5). With respect to powered deployment assembly 80 (FIGS. 3 and 4), for example, upon activation of monopolar activation switch 4b (FIGS. 3 and 4), battery 56 supplied suitable power to create the magnetic field necessary to deploy monopolar assembly 200 (FIGS. 2A-2D). With respect to powered deployment assembly 180 (FIG. 5), as another example, upon activation of switch 3 (FIG. 5), battery 56 provides suitable power to motor 182 is actuate first gear 184, second gear 186, threaded rod 188, and threaded nut 190 to deploy and/or retract monopolar assembly 200 (FIGS. 2A-2D). In some embodiments, battery 56 is a 9V battery. However, it is contemplated that battery 56 may be any energy source suitable for powering powered deployment assembly 80 (FIGS. 3 and 4), powered deployment assembly 180 (FIG. 5), or other suitable powered deployment assembly.

Referring to FIG. 6B in particular, plug housing 52 further includes a housing door 58 for selectively enclosing battery 56 inside compartment 54. Housing door 58 may be selectively secured to housing 52 using any suitable structure such as, for example, mechanical fasteners, friction or snap fit arrangement, tongue and groove configuration, etc. Regardless of the structure securing housing door 58 to housing 52, it is contemplated that the user will be able to access compartment 54 to swap out battery 56 as needed.

Providing a battery 56 within plug housing 52 obviates the need to provide a generator having a suitable energy source for powering the powered deployment assembly 80 (FIGS. 3 and 4), 180 (FIG. 5), e.g., in additional to the bipolar and monopolar energy sources. Thus, forceps 10 may be used in conjunction with any suitable generator that would likewise be capable of powering a similar device having a manual deployment assembly. Further, the positioning of battery 56 within plug housing 52, as opposed to on, in, or adjacent to housing 20, does not add additional weight to forceps 10 (plug housing 52 will typically sit on the table, stand, or other support surface supporting generator "G") and, thus, does not further surgeon fatigue. In addition, the above-detailed configuration enables battery 56 to be readily removed and replaced as necessary.

It is also contemplated that the plug assembly having plug housing 52 with battery 56 therein be configured for powering any other suitable powered mechanism of forceps 10 or any other suitable surgical device. Likewise, powered deployment assemblies 80, 180 are not limited to being powered by battery 56, but may be powered by any other suitable power source.

The use and operation of forceps 10 in both the bipolar mode, e.g., for grasping, treating and/or cutting tissue, and the monopolar mode, e.g., for electrical/electromechanical tissue treatment, is described with reference to FIGS. 1-4 and 6A-6C. The use and operation of forceps 10 is detailed below in conjunction with powered deployment assembly 80. The use and operation of forceps 10 in conjunction with powered deployment assembly 180 (FIG. 5) is similar to that of powered deployment assembly 80, except where specifically contradicted above with respect to the description of powered deployment assembly 180 (FIG. 5).

With respect to the use and operation of forceps 10 in the bipolar mode, reference is made to FIGS. 1 and 2A. Initially, actuator 84 is disposed in its proximal position adjacent proximal portion 86a of guide 86, corresponding to the un-actuated position of powered deployment assembly 80 and the storage position of monopolar assembly 200, wherein insulative sleeve 210 is positioned proximally of jaw members 110, 120, and electrically-conductive tip 224 of energizable member 220 is disposed within insulative groove 126 of jaw flange 124 of jaw member 120. At this point, movable handle 32 is disposed in its initial position such that jaw members 110, 120 are disposed in the spaced-apart position. Further, trigger 62 of trigger assembly 60 remains un-actuated such that the knife remains disposed in its retracted position.

With jaw members 110, 120 disposed in the spaced-apart position (FIG. 2A), end effector assembly 100 may be maneuvered into position such that tissue to be grasped, treated, e.g., sealed, and/or cut, is disposed between jaw members 110, 120. Next, movable handle 32 is depressed, or pulled proximally relative to fixed handle 34 such that jaw member 110 is pivoted relative to jaw member 120 from the spaced-apart position to the approximated position to grasp tissue therebetween, as shown in FIG. 2B. In this approximated position, energy may be supplied, e.g., via activation of bipolar activation switch 4a, to plate 112 of jaw member 110 and/or plate 122 of jaw member 120 and conducted through tissue to treat tissue, e.g., to effect a tissue seal or otherwise treat tissue in the bipolar mode of operation. Once tissue treatment is complete (or to cut untreated tissue), the knife (not shown) may be deployed from within shaft 12 to between jaw members 110, 120, e.g., via actuation of trigger 62 of trigger assembly 60, to cut tissue grasped between jaw members 110, 120.

When tissue cutting is complete, trigger 62 may be released to return the knife (not shown) to the retracted position. Thereafter, movable handle 32 may be released or returned to its initial position such that jaw members 110, 120 are moved back to the spaced-apart position (FIG. 2A) to release the treated and/or divided tissue.

For operation of forceps 10 in the monopolar mode, jaw members 110, 120 are first moved to the approximated position, e.g., by depressing movable handle 32 relative to fixed handle 34. Once the approximated position has been achieved, monopolar assembly 200 may be deployed and activated by transitioning the powered deployment assembly 80 from the un-actuated condition to the actuated condition (FIG. 4). In order to deploy and activate monopolar assembly 200, monopolar activation switch 4b is activated to establish the magnetic field and move actuator 84 to translate distally along guide 86 from the proximal position shown in FIG. 3 to the distal position shown in FIG. 4. This distal translation of actuator 84 (against the bias of biasing member 88) moves insulative sleeve 210 and energizable member 220 distally from their respective storage positions (FIGS. 2A and 2B) to their respective deployed positions (FIG. 2D) relative to housing 20 and shaft 12, thus transitioning monopolar assembly 200 to the deployed position.

More specifically, when monopolar activation switch 4b is activated, deployment circuit "DC" is in a closed condition, thereby allowing current flow from the energy source, e.g., battery 56 or other suitable energy source. As such, the magnetic field is produced around at least a portion of electromagnet 82. As discussed above, the magnetic field acts on actuator 84 such that actuator 84 translates distally towards electromagnet 82 (FIG. 4) against the bias of biasing member 88 to deploy monopolar assembly 200. Once the distal position of actuator 84 is achieved, e.g., at distal portion 86b of guide 86, actuator 84 triggers distal sensor 40b such that distal sensor 40b communicates with electrosurgical generator "G" to initiate the supply of monopolar voltage-current to energizable member 220. In one embodiment, electrosurgical generator "G" continues to supply monopolar voltage-current to energizable member 220 for a duration that monopolar activation switch 4b remains activated. Other additional or alternative energy delivery algorithms are also contemplated.

Upon deactivation, e.g., release, of monopolar activation switch 4b, deployment circuit "DC" changes to an open condition and current flow is stopped. In this condition, there is no longer a magnetic field produced around at least a portion of electromagnet 82 to attract actuator 84. As such, the bias of biasing member 88 urges actuator 84 proximally towards proximal portion 86a of guide 86 to return monopolar assembly 200 to the storage position. When actuator 84 is adjacent proximal sensor 40a and monopolar assembly 200 is in the storage position, sensor 40a communicates with electrosurgical generator "G" to terminate the supply of monopolar voltage-current to energizable member 220. Alternatively, the supply of energy may be terminated as soon as monopolar assembly 200 begins to be retracted from the deployed position, e.g., as soon as actuator 84 departs the distal position.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various drawing figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a housing;
   an energizable member configured to supply electrosurgical energy to tissue, the energizable member movable relative to the housing between a storage position and a deployed position;
   a powered deployment assembly configured to selectively move the energizable member between the storage position and the deployed position, wherein the powered deployment assembly includes a fixed guide and an actuator movably supported within the fixed guide, the actuator coupled to the energizable member and configured to move relative to the fixed guide to selectively move the energizable member between the storage position and the deployed position, the actuator including a ferromagnetic material and the powered deployment assembly including a magnet configured to actuate the actuator, the fixed guide extending between a proximal portion and a distal portion of the surgical instrument and the magnet being fixed to the distal portion of the fixed guide, and wherein the actuator is slidably disposed on the proximal portion of the fixed guide; and
   a cable assembly having a cable coupled to the housing at a first end and having a plug coupled to the cable at a second, opposite end, the cable housing one or more first wires for selectively providing electrosurgical energy to the energizable member, the cable housing one or more second wires for providing power to the powered deployed assembly, the plug configured to house a battery therein for powering the powered deployment assembly via the one or more second wires.

2. The surgical instrument according to claim 1, wherein the magnet is an electromagnet and wherein the energy source in the plug is configured to selectively provide energy to produce a magnetic field around at least a portion of the electromagnet.

3. The surgical instrument according to claim 1, wherein the powered deployment assembly further includes a biasing member disposed between the magnet and the actuator, the biasing member configured to bias the magnet away from the actuator.

4. The surgical instrument according to claim 1, further including a switch assembly operably coupled to the powered deployment assembly and adapted to connect to a source of electrosurgical energy such that when the switch is activated electrosurgical energy is supplied to the energizable member when the energizable member is in the deployed position.

5. The surgical instrument according to claim 1, wherein the powered deployment assembly includes a motor configured to drive movement of the energizable member between the storage position and the deployed position.

6. A surgical instrument, comprising:
   a housing;
   an energizable member configured to supply electrosurgical energy to tissue, the energizable member movable relative to the housing between a storage position and a deployed position;
   a powered deployment assembly configured to selectively move the energizable member between the storage position and the deployed position, the powered deployment assembly including:
      a fixed guide having a proximal portion and a distal portion;
      an electromagnet disposed in the housing and configured to be selectively energizable;
      an actuator disposed in the housing and movable relative to the fixed guide along an axis between the proximal portion and the distal portion of the fixed guide, the actuator operably coupled to the energizable member; and
      a biasing member disposed between the electromagnet and the actuator to bias the electromagnet and actuator apart from one another, wherein energizing the electromagnet moves the actuator distally towards the electromagnet, thereby translating the energizable member to the deployed position; and
   a switch disposed on the housing and operably coupled to the powered deployment assembly for selectively energizing the electromagnet, wherein the electromagnet is fixed to the distal portion of the fixed guide and the actuator is slidably disposed on the proximal portion of the fixed guide.

7. The surgical instrument according to claim 6, wherein the fixed guide includes at least one stopper, the at least one stopper configured to provide for controlled linear motion of the actuator.

8. The surgical instrument according to claim 6, wherein a cable assembly is coupled to the housing at a first end, and has a plug at a second, opposite end, the plug adapted to connect to an energy source for powering the powered deployment assembly.

9. The surgical instrument according to claim 8, wherein the plug houses a battery for powering the powered deployment assembly.

10. The surgical instrument according to claim 6, wherein the switch assembly includes at least one sensor, the at least one sensor adapted to communicate with a source of electrosurgical energy to selectively supply electrosurgical energy to the energizable member when the energizable member is in the deployed position.

* * * * *